US012358953B2

(12) United States Patent
Yoon et al.

(10) Patent No.: US 12,358,953 B2
(45) Date of Patent: Jul. 15, 2025

(54) **ANTIBACTERIAL PROTEIN HAVING LYTIC ACTIVITY TO *Bacillus* GENUS AND METHOD FOR PREPARING THE SAME**

(71) Applicant: iNtRON Biotechnology, Inc., Seongnam-si (KR)

(72) Inventors: Seong Jun Yoon, Seoul (KR); Soo Youn Jun, Seoul (KR); Gi Mo Jung, Seoul (KR); Jin Hee Lee, Seoul (KR); Sang Hyeon Kang, Seoul (KR)

(73) Assignee: iNtRON Biotechnology, Inc., Seongnam-si (KR)

( * ) Notice: Subject to any disclaimer, the term of this patent is extended or adjusted under 35 U.S.C. 154(b) by 588 days.

(21) Appl. No.: 17/908,853

(22) PCT Filed: Mar. 6, 2021

(86) PCT No.: PCT/IB2021/051886
§ 371 (c)(1),
(2) Date: Sep. 1, 2022

(87) PCT Pub. No.: WO2021/181235
PCT Pub. Date: Sep. 16, 2021

(65) Prior Publication Data

US 2023/0212226 A1 Jul. 6, 2023

Related U.S. Application Data

(60) Provisional application No. 62/986,904, filed on Mar. 9, 2020.

(51) Int. Cl.

| | |
|---|---|
| ***C07K 14/00*** | (2006.01) |
| ***A61K 9/20*** | (2006.01) |
| ***A61P 31/04*** | (2006.01) |

(52) U.S. Cl.
CPC ............ *C07K 14/00* (2013.01); *A61K 9/2018* (2013.01); *A61K 9/2045* (2013.01); *A61P 31/04* (2018.01)

(58) Field of Classification Search
CPC ....... C07K 14/00; A61P 31/04; A61K 9/2018; A61K 9/2045
See application file for complete search history.

(56) References Cited

U.S. PATENT DOCUMENTS

| | | | |
|---|---|---|---|
| 8,268,316 B2 | 9/2012 | Hong et al. | |
| 2020/0128856 A1 * | 4/2020 | Martinez ................ | A23K 10/20 |

FOREIGN PATENT DOCUMENTS

| | | |
|---|---|---|
| KR | 20170052946 A | 5/2017 |
| KR | 10-1765393 B1 | 8/2017 |
| WO | 2017061732 A1 | 4/2017 |

OTHER PUBLICATIONS

Park, Sangjin et al., "Characterisation of the antibacterial properties of the recombinant phage endolysins AP50-31 and LysB4 as potent bactericidal agents against *Bacillus anthracis*", Scientific Reports, Jan. 8, 2018 (Online publication date), vol. 8, Article No. 18, pp. 1-11.

* cited by examiner

*Primary Examiner* — Li N Komatsu
(74) *Attorney, Agent, or Firm* — SIMI Law Group, PC

(57) ABSTRACT

An antibacterial protein against *Bacillus* with the amino acid sequence as set forth in SEQ ID NO: 1 is disclosed. Also disclosed is a method of preparing an antibacterial protein against *Bacillus*. The method includes: culturing BL21-pBAD-BAL200 cells, the BL21-pBAD-BAL200 cells including a plasmid that comprising a sequence as set forth in SEQ ID NO: 2; inducing the expression of the antibacterial protein; and purifying the antibacterial protein.

12 Claims, 7 Drawing Sheets

Specification includes a Sequence Listing.

SEQUENCE LISTING

```
<160> NUMBER OF SEQ ID NOS: 2

<210> SEQ ID NO 1
<211> LENGTH: 247
<212> TYPE: PRT
<213> ORGANISM: Artificial sequence
<220> FEATURE:
<223> OTHER INFORMATION: Antibacterial protein BAL200

<400> SEQUENCE: 1

Met Ala Met Ala Leu Gln Thr Leu Ile Asp Lys Ala Asn Arg Lys Leu
1               5                   10                  15

Asn Val Ser Gly Met Arg Lys Asp Val Ala Asp Arg Thr Arg Ala Val
            20                  25                  30

Ile Thr Gln Met His Ala Ser Gly Ile Tyr Ile Cys Val Ala Gln Gly
        35                  40                  45
```

-continued

Trp Arg Ser Phe Ala Glu Gln Asn Ala Leu Tyr Ala Gln Gly Arg Thr
    50                  55                  60

Lys Pro Gly Ser Ile Val Thr Asn Ala Arg Gly Gly Gln Ser Asn His
65                  70                  75                  80

Asn Tyr Gly Val Ala Val Asp Leu Cys Leu Tyr Thr Gln Asp Gly Ser
                85                  90                  95

Asp Val Ile Trp Thr Val Glu Gly Asn Phe Arg Lys Val Ile Ala Ala
            100                 105                 110

Met Lys Ala Gln Gly Phe Lys Trp Gly Gly Asp Trp Val Ser Phe Lys
        115                 120                 125

Asp Tyr Pro His Phe Glu Leu Tyr Asp Val Val Gly Gly Gly Ser Gly
    130                 135                 140

Ser Thr Gly Gly Ser Gly Gly Gly Ser Thr Gly Gly Gly Ser Thr Gly
145                 150                 155                 160

Gly Leu Tyr Asp Ser Ser Trp Phe Thr Lys Glu Thr Gly Thr Phe Val
                165                 170                 175

Thr Asn Thr Ser Ile Lys Leu Arg Thr Ala Pro Phe Thr Ser Ala Asp
            180                 185                 190

Val Ile Ala Thr Leu Pro Ala Gly Ser Pro Val Asn Tyr Asn Gly Phe
        195                 200                 205

Gly Ile Glu Tyr Asp Gly Tyr Val Trp Ile Arg Gln Pro Arg Ser Asn
    210                 215                 220

Gly Tyr Gly Tyr Leu Ala Thr Gly Glu Ser Lys Gly Gly Lys Arg Gln
225                 230                 235                 240

Asn Tyr Trp Gly Thr Phe Lys
                245

<210> SEQ ID NO 2
<211> LENGTH: 4811
<212> TYPE: DNA
<213> ORGANISM: Artificial sequence
<220> FEATURE:
<223> OTHER INFORMATION: BL21-pBAD-BAL200 cell plasmid

<400> SEQUENCE: 2
aagaaaccaa ttgtccatat tgcatcagac attgccgtca ctgcgtcttt tactggctct 60
tctcgctaac caaaccggta accccgctta ttaaaagcat tctgtaacaa agcgggacca 120
aagccatgac aaaaacgcgt aacaaaagtg tctataatca cggcagaaaa gtccacattg 180
attatttgca cggcgtcaca ctttgctatg ccatagcatt tttatccata agattagcgg 240
atcctacctg acgcttttta tcgcaactct ctactgtttc tccatacccg tttttttggg 300
ctagaaataa ttttgtttaa ctttaagaag gagatataca tccatggcaa tggcattaca 360
aactttaatc gacaaggcga accgtaaatt gaacgtttct ggtatgcgta aggacgtagc 420
agaccgtacc cgcgctgtca ttacacaaat gcatgcatcc ggtatttata tctgtgtagc 480
acaaggttgg cgttcgtttg ctgaacagaa cgctttatac gcgcaaggtc gtactaaacc 540
gggtagcatc gtaacaaatg cacgaggcgg acaatcgaac cacaactacg gagtagcggt 600
agacttatgc ttgtacacac aagacggttc tgacgttatc tggacagttg aaggtaattt 660
ccgtaaggtt atcgcagcaa tgaaagcaca aggcttcaaa tggggcggag attgggtttc 720
atttaaagat taccctcact ttgaattgta cgatgtagta ggcggaggct ctggtagcac 780
aggcggttct ggcggaggaa gtacaggagg tggctctaca ggtggactgt acgattctag 840
ctggtttaca aaagagactg gtactttcgt aacaaatact tcaatcaaat tacgtacagc 900

-continued

```
accattcaca agtgcagacg taatcgctac acttccggct ggttctccag ttaactacaa    960
tggcttcggt atcgaatatg atggttacgt ttggattcgt caaccacgta gcaatggtta   1020
cggctatctt gctacaggtg aatctaaagg cggaaaacgt cagaactact ggggtacgtt   1080
caaataagcg gccgcaaggg cgagcttgaa ggtaagccta tccctaaccc tctcctcggt   1140
ctcgattcta cgcgtaccgg tcatcatcac catcaccatt gagtttaaac ggtctccagc   1200
ttggctgttt tggcggatga gagaagattt tcagcctgat acagattaaa tcagaacgca   1260
gaagcggtct gataaaacag aatttgcctg gcggcagtag cgcggtggtc ccacctgacc   1320
ccatgccgaa ctcagaagtg aaacgccgta gcgccgatgg tagtgtgggg tctccccatg   1380
cgagagtagg gaactgccag gcatcaaata aaacgaaagg ctcagtcgaa agactgggcc   1440
tttcgtttta tctgttgttt gtcggtgaac gctctcctga gtaggacaaa tccgccggga   1500
gcggatttga acgttgcgaa gcaacggccc ggagggtggc gggcaggacg cccgccataa   1560
actgccaggc atcaaattaa gcagaaggcc atcctgacgg atggcctttt tgcgtttcta   1620
caaactcttt tgtttatttt tctaaataca ttcaaatatg tatccgctca tgagattatc   1680
aaaaaggatc ttcacctaga tccttttaaa ttaaaaatga agttttaaat caatctaaag   1740
tatatatgag taaacttggt ctgacagtta ggcgtcgctt ggtcggtcat ttcgaacccc   1800
agagtcccgc tcagaagaac tcgtcaagaa ggcgatagaa ggcgatgcgc tgcgaatcgg   1860
gagcggcgat accgtaaagc acgaggaagc ggtcagccca ttcgccgcca agctcttcag   1920
caatatcacg ggtagccaac gctatgtcct gatagcggtc cgccacaccc agccggccac   1980
agtcgatgaa tccagaaaag cggccatttt ccaccatgat attcggcaag caggcatcgc   2040
catgtgtcac gacgagatcc tcgccgtcgg gcatgcgcgc cttgagcctg gcgaacagtt   2100
cggctggcgc gagcccctga tgctcttcgt ccagatcatc ctgatcgaca agaccggctt   2160
ccatccgagt acgtgctcgc tcgatgcgat gtttcgcttg gtggtcgaat gggcaggtag   2220
ccggatcaag cgtatgcagc cgccgcattg catcagccat gatggatact ttctcggcag   2280
gagcaaggtg agatgacagg agatcctgcc ccggcacttc gcccaatagc agccagtccc   2340
ttcccgcttc agtgacaacg tcgagcacag ctgcgcaagg aacgcccgtc gtggccagcc   2400
acgatagccg cgctgcctcg tcctgcagtt cattcagggc accggacagg tcggtcttga   2460
caaaaagaac cgggcgcccc tgcgctgaca gccggaacac ggcggcatca gagcagccga   2520
ttgtcagttg tgcccagtca tagccgaata gcctctccac ccaagcggcc ggagaacctg   2580
cgtgcaatcc atcttgttca atcatactct tcctttttca atattattga agcatttatc   2640
agggttattg tctcatgacc aaaatccctt aacgtgagtt ttcgttccac tgagcgtcag   2700
accccgtaga aaagatcaaa ggatcttctt gagatccttt ttttctgcgc gtaatctgct   2760
gcttgcaaac aaaaaaacca ccgctaccag cggtggtttg tttgccggat caagagctac   2820
caactctttt tccgaaggta actggcttca gcagagcgca gataccaaat actgtccttc   2880
tagtgtagcc gtagttaggc caccacttca agaactctgt agcaccgcct acatacctcg   2940
ctctgctaat cctgttacca gtggctgctg ccagtggcga taagtcgtgt cttaccgggt   3000
tggactcaag acgatagtta ccggataagg cgcagcggtc gggctgaacg gggggttcgt   3060
gcacacagcc cagcttggag cgaacgacct acaccgaact gagataccta cagcgtgagc   3120
tatgagaaag cgccacgctt cccgaaggga gaaaggcgga caggtatccg gtaagcggca   3180
gggtcggaac aggagagcgc acgagggagc ttccaggggg aaacgcctgg tatctttata   3240
```

-continued

```
gtcctgtcgg gtttcgccac ctctgacttg agcgtcgatt tttgtgatgc tcgtcagggg   3300

ggcggagcct atggaaaaac gccagcaacg cggccttttt acggttcctg gcattttgct   3360

ggccttttgc tcacatgttc tttcctgcgt tatcccctga ttctgtggat aaccgtatta   3420

ccgcctttga gtgagctgat accgctcgcc gcagccgaac gaccgagcgc agcgagtcag   3480

tgagcgagga agcggaagag cgcctgatgc ggtattttct ccttacgcat ctgtgcggta   3540

tttcacaccg catatggtgc actctcagta caatctgctc tgatgccgca tagttaagcc   3600

agtatacact ccgctatcgc tacgtgactg ggtcatggct gcgccccgac acccgccaac   3660

acccgctgac gcgccctgac gggcttgtct gctcccggca tccgcttaca gacaagctgt   3720

gaccgtctcc gggagctgca tgtgtcagag gttttcaccg tcatcaccga aacgcgcgag   3780

gcagcagatc aattcgcgcg cgaaggcgaa gcggcatgca taatgtgcct gtcaaatgga   3840

cgaagcaggg attctgcaaa ccctatgcta ctccgtcaag ccgtcaattg tctgattcgt   3900

taccaattat gacaacttga cggctacatc attcactttt tcttcacaac cggcacggaa   3960

ctcgctcggg ctggccccgg tgcatttttt aaatacccgc gagaaataga gttgatcgtc   4020

aaaaccaaca ttgcgaccga cggtggcgat aggcatccgg gtggtgctca aaagcagctt   4080

cgcctggctg atacgttggt cctcgcgcca gcttaagacg ctaatcccta actgctggcg   4140

gaaaagatgt gacagacgcg acggcgacaa gcaaacatgc tgtgcgacgc tggcgatatc   4200

aaaattgctg tctgccaggt gatcgctgat gtactgacaa gcctcgcgta cccgattatc   4260

catcggtgga tggagcgact cgttaatcgc ttccatgcgc cgcagtaaca attgctcaag   4320

cagatttatc gccagcagct ccgaatagcg cccttcccct tgcccggcgt taatgatttg   4380

cccaaacagg tcgctgaaat gcggctggtg cgcttcatcc gggcgaaaga accccgtatt   4440

ggcaaatatt gacggccagt taagccattc atgccagtag gcgcgcggac gaaagtaaac   4500

ccactggtga taccattcgc gagcctccgg atgacgaccg tagtgatgaa tctctcctgg   4560

cgggaacagc aaaatatcac ccggtcggca aacaaattct cgtccctgat tttcaccac   4620

cccctgaccg cgaatggtga gattgagaat ataacctttc attcccagcg gtcggtcgat   4680

aaaaaaatcg agataaccgt tggcctcaat cggcgttaaa cccgccacca gatgggcatt   4740

aaacgagtat cccggcagca ggggatcatt ttgcgcttca gccatacttt tcatactccc   4800

gccattcaga g                                                         4811
```

ANTIBACTERIAL PROTEIN HAVING LYTIC ACTIVITY TO *Bacillus* GENUS AND METHOD FOR PREPARING THE SAME The present application claims priority to U.S. Provisional Patent Application No. 62/986,904, filed on Mar. 9, 2020, which is incorporated by reference for all purposes as if fully set forth herein.

BACKGROUND OF THE INVENTION

Field of the Invention

The present invention is related to an antibacterial protein having the lytic activity to *Bacillus*, more specifically, the present invention relates to a *Bacillus* genus-specific antibacterial protein (BAL200), a pharmaceutical composition including the same, and a method of preparing the same.

Discussion of the Related Art

The genus *Bacillus* is Gram-positive spore-forming mostly motile bacteria that include more than 260 species. Some *Bacillus* species, such as *Bacillus subtilis* and *Bacillus laevolacticus*, are practically beneficial enough to be used as probiotics, while others cause clinically serious infections including bacteremia, septicemia and cerebromeningitis. Well-known harmful *Bacillus* species include *Bacillus cereus, Bacillus circulans, Bacillus laevolacticus, Bacillus licheniformis, Bacillus megaterium, Bacillus pumilus*, and *Bacillus anthracis. Bacillus cereus* is widely known as the bacteria causing food poisoning together with *E. coli, Salmonella* and *Staphylococcus aureus*. Also, *Bacillus cereus* and *Bacillus licheniformis* are known as common causes of bovine mastitis. *Bacillus anthracis* causes the infectious "anthrax" or "anthrax infection." Most mammals are susceptible to anthrax, including cows, sheep, goats, mules and dogs as well as humans eating meat from infected animals. The incubation period for anthrax is 1-5 days. Within 24 hours following the onset of severe acute and acute symptoms, respectively, anthrax may lead to death 1-2 hours. Generally, symptoms of anthrax include sudden high fever, dyspnea and severe depression. In animals, the main route of anthrax infection is the oral infection via soil or pasturage contaminated by *Bacillus anthracis*, while the cutaneous anthrax through wounds or the inhalation anthrax often occurs. Blood-sucking insects may act as the source of infection as well.

Infections caused by *Bacillus* are usually treated with antibiotics. Recently, however, *Bacillus* bacteria have increasingly developed resistance to antibiotics, thereby the therapeutic effects of antibiotics are reduced. To effectively address the infections caused by *Bacillus* resistant to existing antibiotics, new antibiotic/antibacterial substances are needed. Notably, it is urgent to develop pharmaceuticals that can provide the rapid therapeutic effects.

The present inventors have proposed utilizing the antibacterial protein B4 (Korean Patent Registration No. 10-1765393) as an option to provide the rapid therapeutic effects. The antibacterial protein B4 has superior antibacterial activity against several *Bacillus anthracis* strains including *Bacillus anthracis* ATCC 14578, *Bacillus anthracis* delta-Sterne, *Bacillus anthracis* Sterne, *Bacillus anthracis* HS, *Bacillus anthracis* HY and *Bacillus anthracis* KJ (Korean Patent Registration No. 10-1765393).

That being said, the antibacterial protein B4 needs reinforcing in many aspects to be used more effectively as a pharmaceutical drug delivering superior pharmaceutical properties. Given the overarching issue relevant to the development of protein drugs is immunogenicity associated with the immune response to in vivo administration, it is essential to reduce the immunogenicity. The anti-drug antibodies (ADAs) produced in response to the administration of drugs contain neutralizing ADAs, which offset the benefits of administered drugs, reduce or negate their efficacy, shorten the survival time of drugs in the body, or may cause acute immune responses or autoimmune diseases. Therefore, it is critical to minimize the immunogenicity in developing recombinant protein drugs. In addition, it is necessary to reduce the size of recombinant protein drugs to extend their effects even to biofilm bacteria.

SUMMARY OF THE INVENTION

Accordingly, the present invention has been made keeping in mind the problems encountered in the related art and is intended to solve such problems.

In one embodiment, the present invention discloses an antibacterial protein against *Bacillus* with the amino acid sequence as set forth in SEQ ID NO: 1.

In another embodiment, the antibacterial protein includes 247 amino acids and has a molecular weight of 26.5 kDa.

In another embodiment, the antibacterial protein has lytic activity against *Bacillus*.

In another embodiment, the antibacterial protein has lytic activity against *Bacillus anthracis. Bacillus cereus, Bacillus circulans, Bacillus laevolacticus, Bacillus licheniformis, Bacillus megaterium*, and *Bacillus pumilus*.

In another embodiment, the antibacterial protein has no lytic activity against *Salmonella, E. coli, Enterococcus faecalis*, and *Staphylococcus aureus*.

In another embodiment, the present invention discloses a pharmaceutical composition that includes the antibacterial protein or any antibacterially active fragment thereof and treats the diseases caused by *Bacillus* bacteria. The disease is a selected one from, but not limited to, the group consisting of anthrax, food poisoning, bacteremia, septicemia, toxemia and cerebromeningitis.

In another embodiment, the antibacterial protein has a concentration of 0.1-50 mg/mL.

In another embodiment, pharmaceutical composition further includes 10 mM L-Histidine, 0.1% Polysorbate 80, and 5% Sorbitol.

In another embodiment, the pharmaceutical composition is used as food additives, antibiotics, disinfectants, and germicides.

In another embodiment, the present invention discloses a method of preparing an antibacterial protein against *Bacillus*. The method includes: culturing BL21-pBAD-BAL200 cells, the BL21-pBAD-BAL200 cells including a plasmid that comprising a sequence as set forth in SEQ ID NO: 2; inducing the expression of the antibacterial protein; and purifying the antibacterial protein.

In another embodiment, the antibacterial protein has the amino acid sequence as set forth in SEQ ID NO: 1.

In another embodiment, the antibacterial protein has a purity of 90% or more.

It is to be understood that both the foregoing general description and the following detailed description are exemplary and explanatory and are intended to provide further explanation of the invention as claimed.

Advantageous Effects of Invention

In accordance with the present invention, it is possible to use the antibacterial protein which decreases the immunogenicity and innovatively addresses the issue of compromising the efficacy of drugs or the safety issue attributable to immunogenicity. Additionally, it can be used for effectively treating biofilm bacteria. Also, the pharmaceutical composition of the present invention is possibly effective against *Bacillus* genus resistant to existing antibiotics or antibacterial substances. At the same time, the *Bacillus* genus-specific antibacterial protein BAL200 of the present invention does not affect the normal resident flora but *Bacillus* genus, minimizing any adverse effects resulting from the use of the pharmaceutical composition containing the antibacterial protein BAL200 as the active ingredient, in comparison to existing antibiotics that would exert several adverse effects on beneficial bacteria in the body.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

In FIG. 1, the lane M is the protein size marker.

In FIG. 2, (–) is the negative control without BAL200, while (+) denotes the experimental group which antibacterial protein BAL200 is added. The horizontal and vertical axes are time (min) and absorbance at 600 nm, respectively.

In FIG. 3, (–) is the negative control without BAL200, while (+) denotes the experimental group which antibacterial protein BAL200 is added. The horizontal and vertical axes are time (min) and absorbance at 600 nm, respectively.

In FIG. 4, (–) is the negative control without BAL200, while (+) denotes the experimental group which antibacterial protein BAL200 is added. The horizontal and vertical axes are time (min) and absorbance at 600 nm, respectively.

In FIG. 5, (–) is the negative control without BAL200, while (+) denotes the experimental group which antibacterial protein BAL200 is added. The horizontal and vertical axes are time (min) and absorbance at 600 nm, respectively.

In FIG. 6, (–) is the negative control without BAL200, while (+) denotes the experimental group which antibacterial protein BAL200 is added. The horizontal and vertical axes are time (min) and absorbance at 600 nm, respectively.

In FIG. 7, (–) is the negative control without BAL200, while (+) denotes the experimental group which antibacterial protein BAL200 is added. The horizontal and vertical axes are time (min) and absorbance at 600 nm, respectively.

In FIG. 8, (–) is the negative control without BAL200, while (+) denotes the experimental group which antibacterial protein BAL200 is added. The horizontal and vertical axes are time (min) and absorbance at 600 nm, respectively.

In FIG. 9, (–) is the negative control without BAL200, while (+) denotes the experimental group which antibacterial protein BAL200 is added. The horizontal and vertical axes are time (min) and absorbance at 600 nm, respectively.

In FIG. 10, (–) is the negative control without BAL200, while (+) denotes the experimental group which antibacterial protein BAL200 is added. The horizontal and vertical axes are time (min) and absorbance at 600 nm, respectively.

In FIG. 11, (–) is the negative control without BAL200, while (+) denotes the experimental group which antibacterial protein BAL200 is added. The horizontal and vertical axes are time (min) and absorbance at 600 nm, respectively.

In FIG. 12, (–) is the negative control without BAL200, while (+) denotes the experimental group which antibacterial protein BAL200 is added. The horizontal and vertical axes are time (min) and absorbance at 600 nm, respectively.

In FIG. 13, (–) is the negative control without BAL200, while (+) denotes the experimental group which antibacterial protein BAL200 is added. The horizontal and vertical axes are time (min) and absorbance at 600 nm, respectively.

DETAILED DESCRIPTION OF THE ILLUSTRATED EMBODIMENTS

Figure 1:
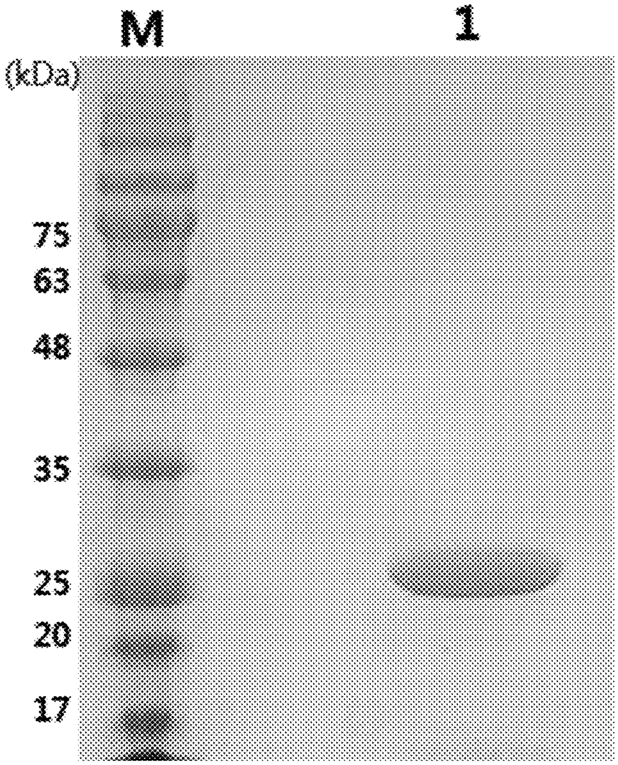
FIG. 1 is an electrophoretic image showing the isolated *Bacillus* genus-specific antibacterial protein BAL200, characterized by the amino acid sequence as set forth in SEQ ID NO: 1, in the form of a recombinant protein.
Figure 2:
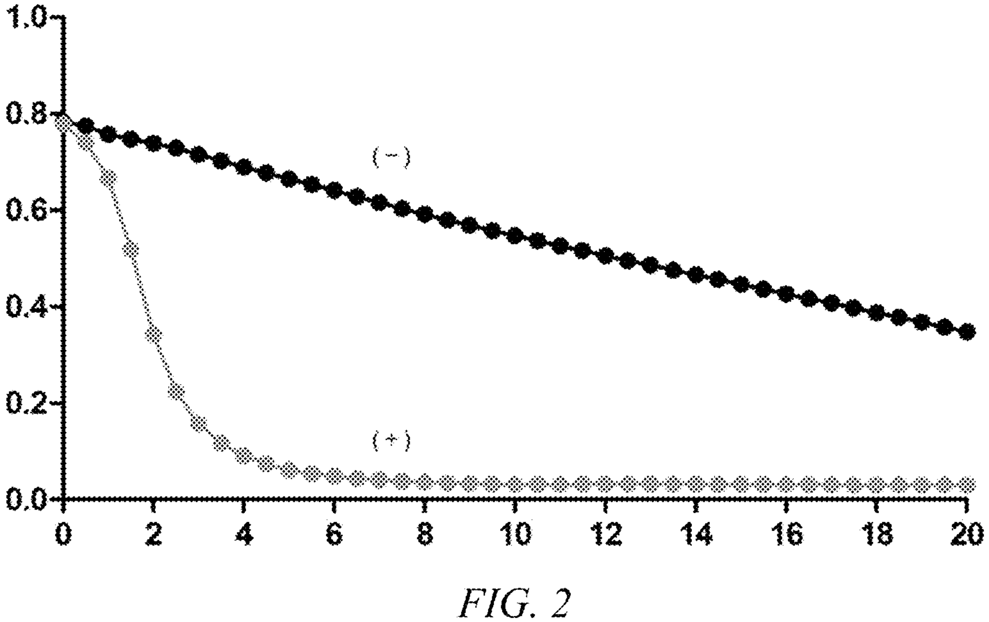
FIG. 2 shows the experimental result of the turbidity reduction assay of *Bacillus cereus*.
Figure 3:
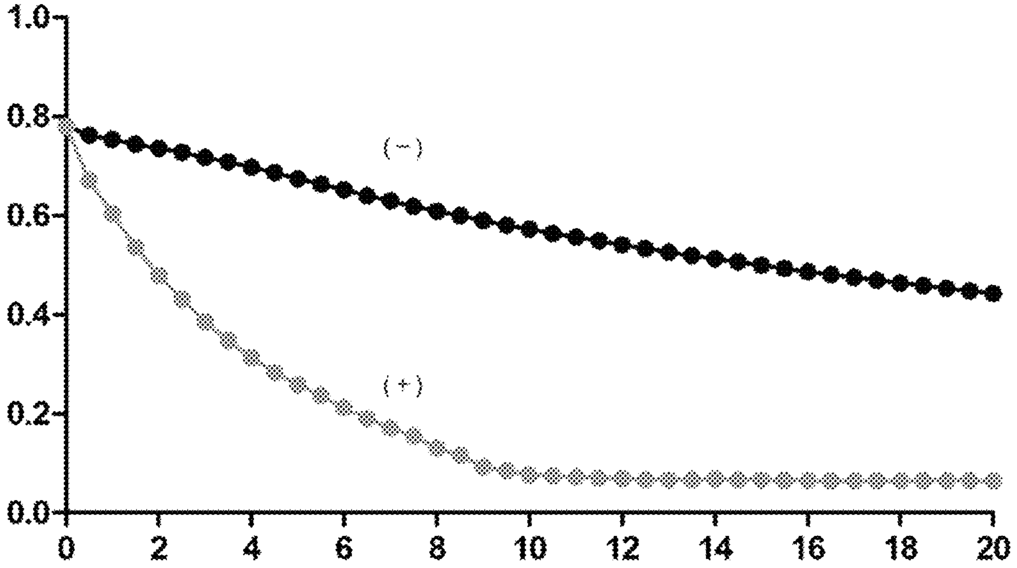
FIG. 3 shows the experimental result of the turbidity reduction assay of *Bacillus circulans*.
Figure 4:
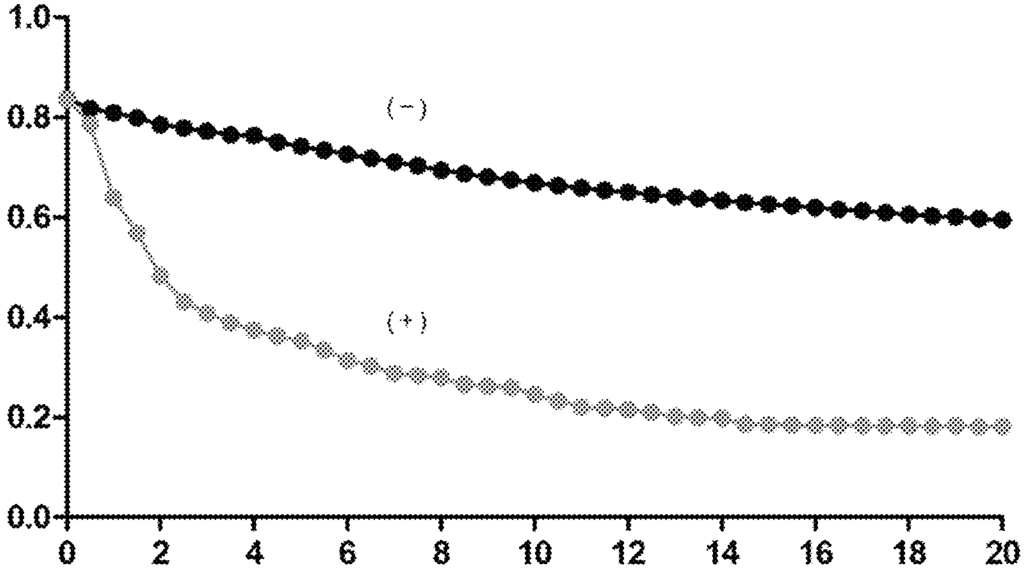
FIG. 4 shows the experimental result of the turbidity reduction assay of *Bacillus laevolacticus*.
Figure 5:
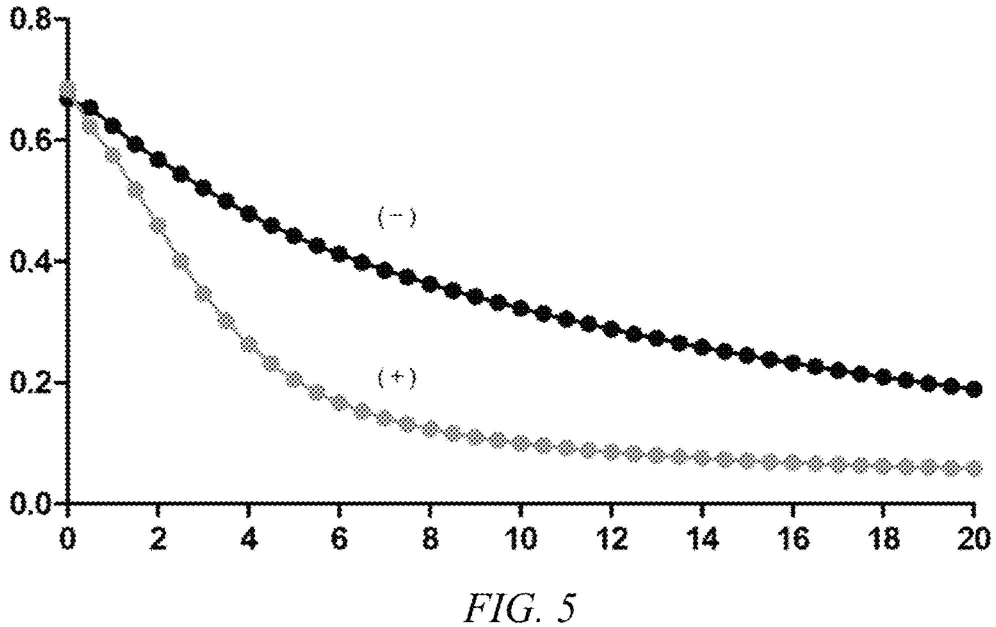
FIG. 5 shows the experimental result of the turbidity reduction assay of *Bacillus licheniformis*.
Figure 6:
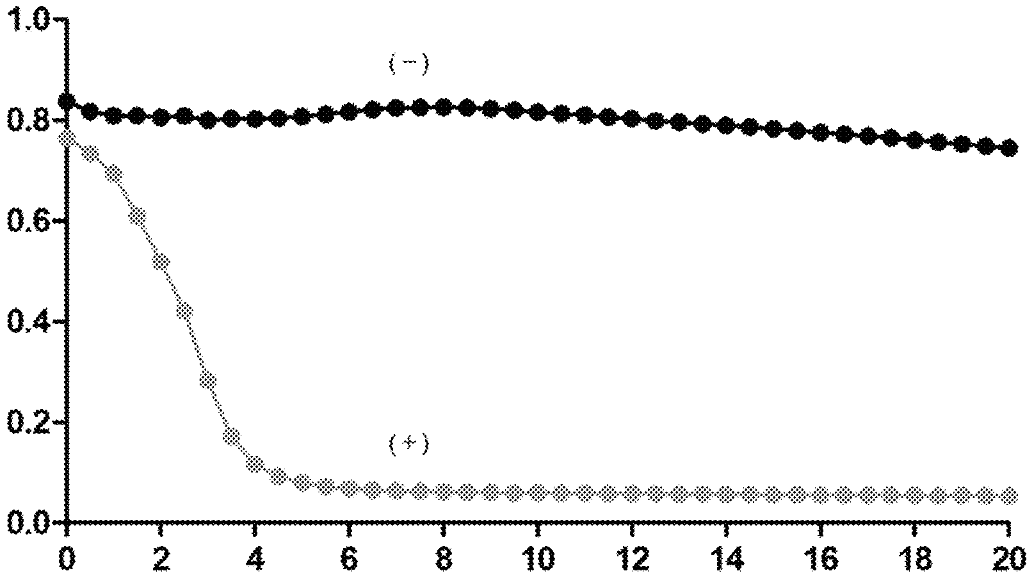
FIG. 6 shows the experimental result of the turbidity reduction assay of *Bacillus megaterium*.
Figure 7:
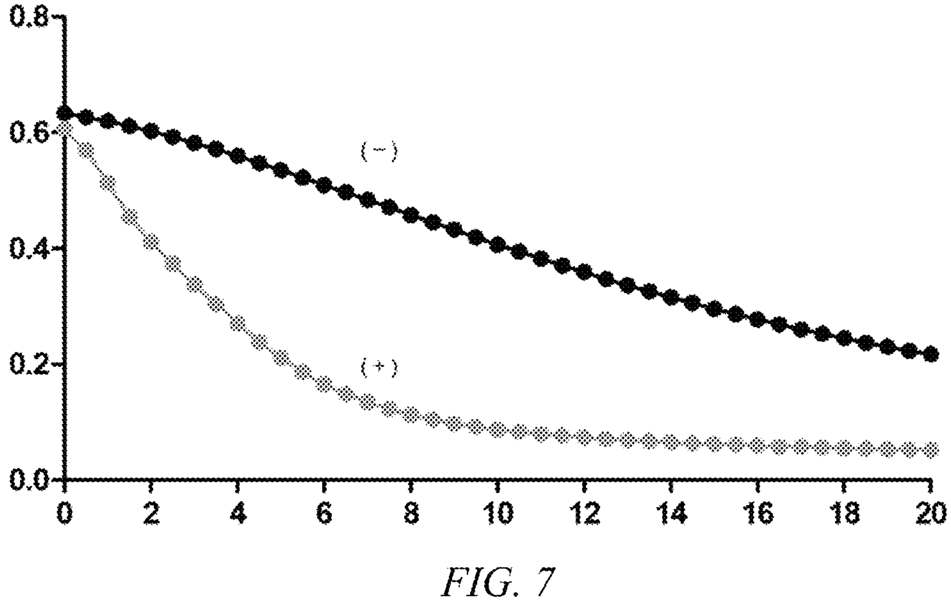
FIG. 7 shows the experimental result of the turbidity reduction assay of *Bacillus pumilus*.
Figure 8:
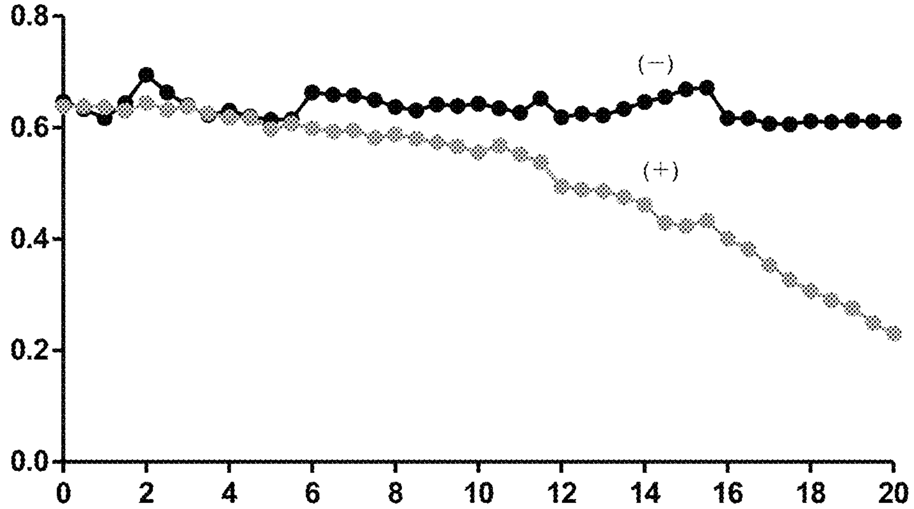
FIG. 8 shows the experimental result of the turbidity reduction assay of *Bacillus anthracis* Ames.
Figure 9:
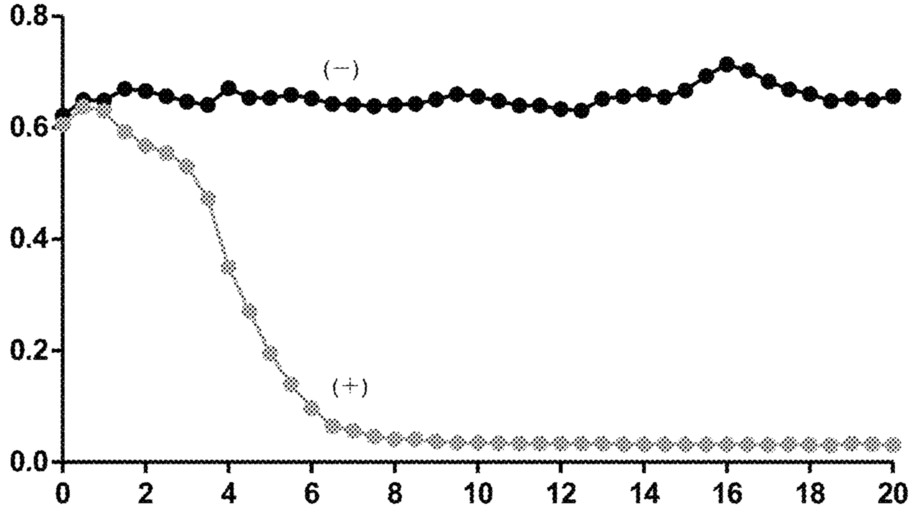
FIG. 9 shows the experimental result of the turbidity reduction assay of *Bacillus anthracis* Sterne.
Figure 10:
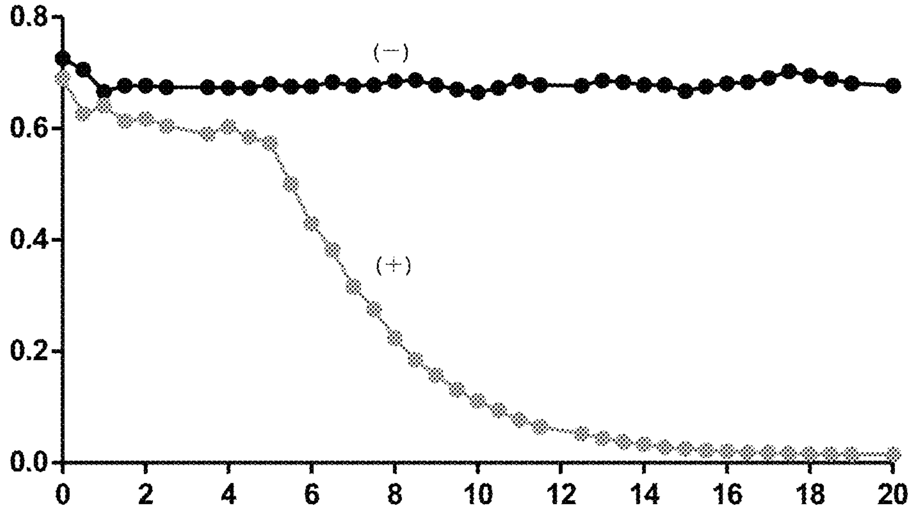
FIG. 10 shows the experimental result of the turbidity reduction assay of *Bacillus anthracis* A0102.
Figure 11:
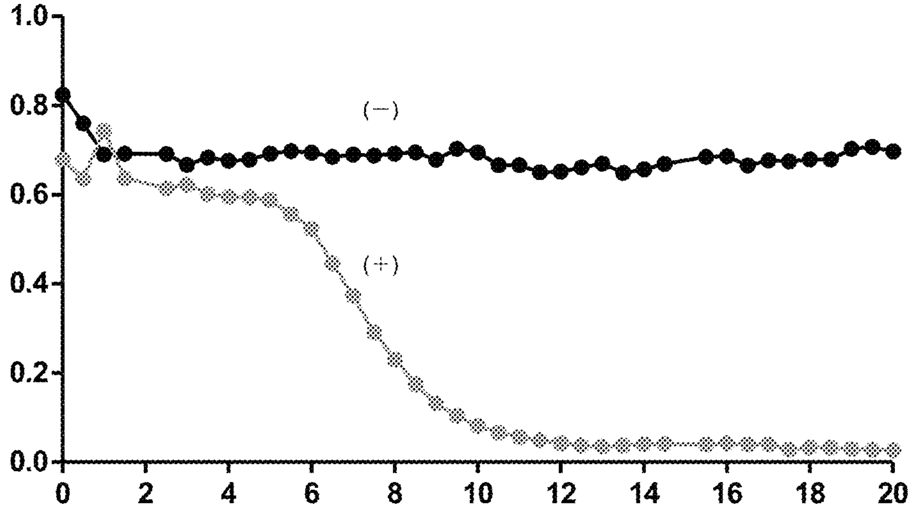
FIG. 11 shows the experimental result of the turbidity reduction assay of *Bacillus anthracis* 1890A Clean Earth.
Figure 12:
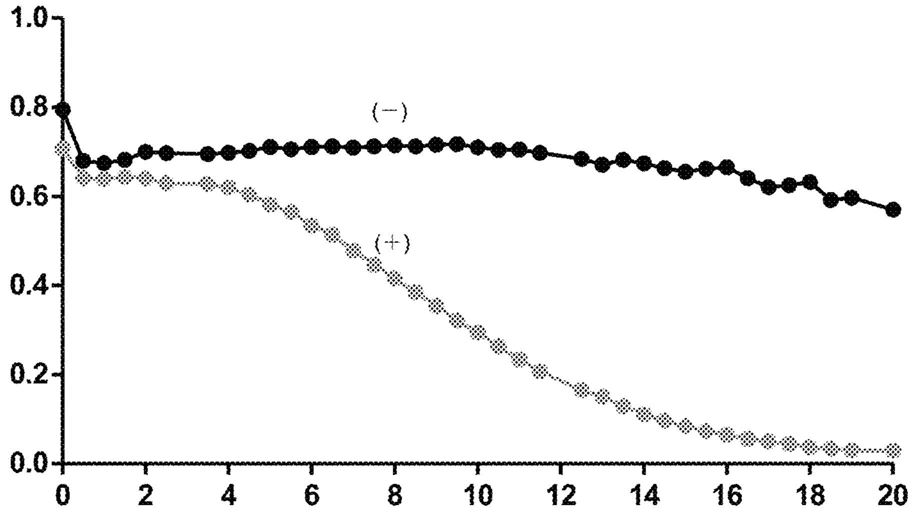
FIG. 12 shows the experimental result of the turbidity reduction assay of *Bacillus anthracis* A0341.
Figure 13:
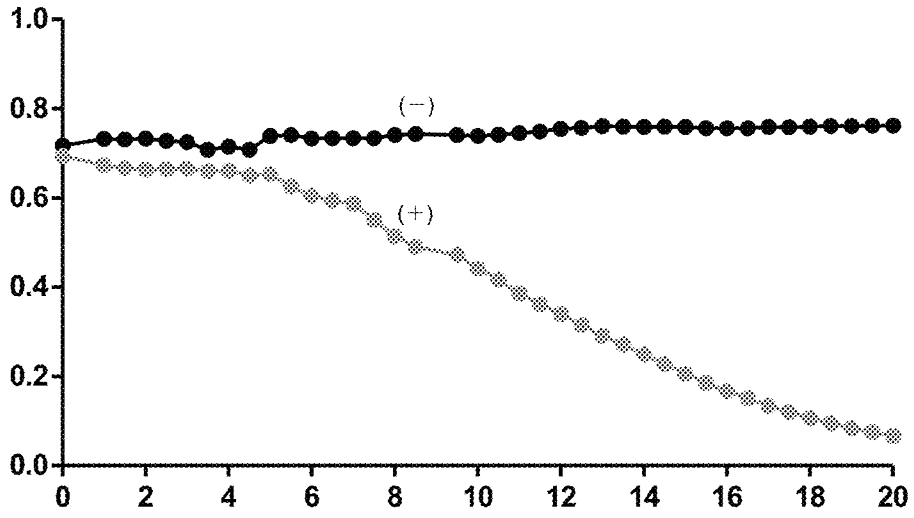
FIG. 13 shows the experimental result of the turbidity reduction assay of *Bacillus anthracis* A0402.

Reference will now be made in detail to embodiments of the present invention, example of which is illustrated in the accompanying drawings.

Thus, in accordance with one aspect of the present invention, there is provided the amino acid sequence of antibacterial protein BAL200 which has the lytic activity specific to *Bacillus* genus. More specifically, the amino acid sequence set forth in SEQ ID NO: 1 is provided. Having the specific lytic activity to *Bacillus* genus, the antibacterial protein BAL200 includes 247 amino acid residues, and has the molecular weight of approximately 26.5 kDa.

The amino acid sequence set forth in SEQ ID NO: 1 may explicitly and partially be modified by those skilled in the art using the disclosed contents. The said modification includes the partial substitution, addition and deletion of the amino acid sequence. That being said, it is most desirable to apply correspondingly the amino acid sequence set forth in SEQ ID NO: 1 as disclosed in the present invention.

Also, the present invention provides a BL21-pBAD-BAL200 strain available to produce the antibacterial protein BAL200 of which the amino acid sequence is set forth in SEQ ID NO: 1. The BL21-pBAD-BAL200 strain was developed by the present inventors and was deposited in the Korean Collection for Type Cultures (KCTC) on Nov. 24, 2019 (Receipt No.: KCTC 14043BP).

Also, in accordance with another aspect of the present invention, the present invention provides a pharmaceutical composition. The active ingredient of the pharmaceutical composition is the antibacterial protein BAL200 which the amino acid sequence set forth in SEQ ID NO: 1 and can effectively treat infections caused by *Bacillus* genus.

As the active ingredient of the pharmaceutical composition of the present invention, the antibacterial protein BAL200 is able to specifically lyse *Bacillus* genus, and effective for treating a range of diseases caused by *Bacillus* genus. Therefore, the pharmaceutical composition of the present invention can treat the diseases caused by *Bacillus* genus. Hence, the pharmaceutical composition of the present invention may be used as antibiotics, disinfectants, germicides and therapeutic drugs, and treat the diseases caused by *Bacillus* genus. Moreover, it is possibly applicable to treating the infections caused by *Bacillus anthracis* in the event of bio-terrorism or bio-wars.

Also, in accordance with another aspect of the present invention, the present invention provides the treatment methods for various diseases caused by *Bacillus* genus, which methods comprise the administration of the specific antibacterial protein BAL200 which is specific to *Bacillus* genus and has amino acid sequence set forth in SEQ ID NO: 1.

Here, the "diseases caused by *Bacillus* genus" collectively refer to the symptoms including fever and dyspnea by infections caused by *Bacillus* genus. The terms "prevention" and "inhibition" used in this specification refer to (i) preventing infections caused by *Bacillus* genus; and (ii) inhibiting the infections caused by *Bacillus* genus from developing into diseases. Also, the term "treating" or "treatment" refers to all actions taken to inhibit the diseases caused by *Bacillus* genus and relieve relevant pathological conditions.

The pharmaceutically acceptable carriers contained in the pharmaceutical composition of the present invention are ordinarily used in preparations, including but not limited to lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methylcellulose, methyl-hydroxybenzoate, propyl hydroxybenzoate, talc, magnesium stearate and mineral oil. In addition to the foregoing ingredients, the pharmaceutical composition of the present invention may include lubricating, wetting, sweetening, flavouring, emulsifying, suspending and preservative agents.

The pharmaceutical composition of the present invention may be administered either orally or non-orally. The non-oral administration may include intravenous, intraperitoneal, intramuscular, subcutaneous or local administration, as well as application or spraying on affected areas.

The pharmaceutical composition of the present invention can be formulated in unit volumes using pharmaceutically acceptable carriers/bulking agents with reference to the method that can be implemented with ease by those skilled in the art of the present invention, or in multi-volume containers. The formulation may take the form of solutions in oil or aqueous media, suspensions or emulsions, or of extracts, powder, granules, tablets or capsules, and may additionally include dispersants or stabilizers.

Also, the appropriate dosage for applying, spraying and administering the foregoing pharmaceutical composition varies with such factors as formulation, administration, age, body weight, severity of symptoms, foods, administration time, administration routes, discharge speed and susceptibility in response. Usually, skilled physicians or veterinarians may decide and prescribe with ease the dosage effective for desired treatments.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Manufacturing of *Bacillus* Genus-Specific Antibacterial Protein BAL200

*Bacillus* genus-specific antibacterial protein BAL200 was prepared as follows. In this example, a BL21-pBAD-BAL200 strain was used as the production strain. Note that, the BL21-pBAD-BAL200 strain was deposited in the KCTC Biological Resource Center on Nov. 24, 2019 (Receipt No.: KCTC 14043BP). The production strain BL21-pBAD-BAL200 has a plasmid that includes the genetic sequence set forth in SEQ ID NO: 2.

20 μl of the BL21-pBAD-BAL200 was added to 20 ml of the LB medium (Tryptone 10 g/L, Yeast extract 5 g/L, Sodium chloride 10 g/L) with kanamycin (50 μg/ml) and inoculated prior to a shaking culture at 37° C. for 6~7 hours. The 20 μl of the culture solution was inoculated into 200 ml of the LB medium with kanamycin (50 μg/ml) prior to an overnight shaking culture at 37° C. The next day, the overnight culture solution was added to the culture medium containing 5 L of the LB medium with kanamycin (50 μg/ml) until the OD600 (absorbance at 600 nm) reached 0.1. Then, it was cultured at 37° C. at an agitation of 200 rpm under an aeration condition of 5 L/min. Once the cell concentration reached 0.5 in reference to the absorbance at 600 nm, L-arabinose was added until the final concentration reached 0.2% to induce the expression of antibacterial protein BAL200 characterized by the amino acid sequence set forth in SEQ ID NO: 1, before an additional culture for 4 hours.

Upon completion of the culture, the cell culture solution underwent a centrifugation at 6,000 rpm for 10 minutes at 4° C., and then the cell pellet was harvested. The collected cell pellet was suspended in 200 ml of the 20 mM Tris-HCl (pH 8.0) buffer. The cells in the prepared suspension were lysed with sonication, where 3-second on/3-second off pulses were alternated for 15 minutes to disrupt the cells in an ice bath.

After the cell lysis, the lysate solution was centrifuged at 13,000 rpm for 20 minutes at 4° C. to get the supernatant, which was in turn purified through the conventional cation-exchange chromatography.

Briefly, the purification process was conducted as follows. In this example, 5 ml of HiTrap™ SP HP (GE Healthcare, Inc.) was used as the cation-exchange resin. The column was pre-equilibrated with the buffer A (20 mM Tris-HCl, 10 mM sodium chloride, pH 8.0) prior to the chromatography. Once the sample was loaded onto the column, the buffer A (10 Column Volume) was flushed at the flow rate of 4 ml/min for washing. After the washing, the chromatography was performed under the condition where the concentration gradient from buffer A to buffer B (20 mM Tris-HCl, 500 mM sodium chloride, pH 8.0) shifted from 0% to 100%. In the process, the elution fractions containing the antibacterial protein BAL200 were obtained. Also, more than 90% purity of the antibacterial protein BAL200 was obtained through the process. FIG. 1 shows the electrophoretic result of the antibacterial protein BAL200 purified in the chromatography process.

Example 2: Preparation of Pharmaceutical Composition Containing *Bacillus* Genus-Specific Antibacterial Protein BAL200

In this example, we prepared the pharmaceutical composition containing the *Bacillus* genus-specific antibacterial protein BAL200 manufactured in Example 1 as the active ingredient. The composition presented in this Example is just one of applicable compositions and cannot be said to be exhaustive.

We prepared multiple compositions using different type of buffers as well as different kinds of stabilizers and additives applicable to pharmaceutical compositions, to explore the composition that could provide an industrially viable stability once the antibacterial protein BAL200 is added. Here, in selecting the buffer, stabilizers and additives, we primarily took into account if these ingredients are pharmaceutically allowed in compliance with the acceptance criteria for medical substances, and the isoelectric points of antibacterial protein BAL200.

More specifically, in the stability test, the resistance degree to physical stress including a 2-hour agitation at 2,500 rpm and 16-hour heating at 40° C. was compared with two weeks short-term storage stability. The stability assessment involved the analysis of absorbance measurements and high performance liquid chromatography (HPLC). As a result, the composition shown in Table 1 below was selected as the formulation appropriate for the antibacterial protein BAL200.

TABLE 1

| | Ingredients |
|---|---|
| Composition | 10 mM L-Histidine, 0.1% Polysorbate 80, 5% Sorbitol, pH 6.0 |

To get the final pharmaceutical composition, buffer exchange of antibacterial protein BAL200 sample obtained in Example 1 was performed with the buffer as per the composition shown in Table 1, and then the final concentration of antibacterial protein BAL200 was adjusted to 5 mg/ml.

Example 3: Assessing Lytic Activity of *Bacillus* Genus-Specific Antibacterial Protein BAL200

Using the pharmaceutical composition (5 mg/ml) prepared in Example 2, we assessed the lytic activity of *Bacillus* genus-specific antibacterial protein BAL200 against various *Bacillus* genus bacteria. The *Bacillus* species used for this assessment of lytic activity were pathogenic *Bacillus cereus, Bacillus circulans, Bacillus laevolacticus, Bacillus licheniformis, Bacillus megaterium* and *Bacillus pumilus*, as outlined in Table 2 below.

TABLE 2

| Species | Strain | Source |
|---|---|---|
| *Bacillus cereus* | ATCC 4342 | ATCC |
| *Bacillus circulans* | KCTC 3004 [ATCC 21783] | KCTC |
| *Bacillus laevolacticus* | KCTC 3117 | KCTC |
| *Bacillus licheniformis* | KCOM 1491 | KCOM |
| *Bacillus megaterium* | KCTC 2178 [ATCC 10778] | KCTC |
| *Bacillus pumilus* | KCTC 3713 | KCTC |

Meanwhile, to assess the lytic activity to other bacterial species in addition to the *Bacillus* species, 3 strains of *Salmonella,* 2 strains of *E. coli,* 2 strains of *Streptococcus mutans,* 3 strains of *Enterococcus faecalis*, and 2 strains of *Staphylococcus aureus* were included in the experiment.

The turbidity reduction assay was used to assess the lytic activity. The experimental method of the turbidity reduction assay is described below. The bacteria were suspended in normal saline until the absorbance at 600 nm reached around 0.8. Then, 0.1 ml of the diluted solution (BAL200 concentration: 5 μg/ml) of the pharmaceutical composition prepared in Example 2 was added to the suspension (0.9 ml). After that, the absorbance at 600 nm was measured for 20 minutes.

According to this experimental result, *Bacillus* genus-specific antibacterial protein BAL200 exhibited the lytic activity only against *Bacillus* bacteria as expected, and had no lytic activity to other bacteria tested. This result confirmed the *Bacillus* genus-specific lytic activity of the protein of the present invention. The experimental results of *Bacillus* bacteria are shown in FIGS. 2~7. In the turbidity reduction assay used to assess the lytic activity, rapid lytic activity was observed. No pre-existing antibiotics provide such rapid lytic activity as manifested in the present invention.

These results prove that the *Bacillus* genus-specific antibacterial protein BAL200 of the present invention is able to lyse and eventually kill *Bacillus* bacteria. This antibacterial property suggests the pharmaceutical composition containing *Bacillus* genus-specific antibacterial protein BAL200 is applicable to killing *Bacillus* bacteria in infections caused by *Bacillus* species, and to treating such infections in the same manner as conventional antibiotics.

Example 4: Assessing Biofilm Eradication Efficacy of *Bacillus* Genus-Specific Antibacterial Protein BAL200

Using the pharmaceutical composition (5 mg/ml) prepared in Example 2, we assessed the biofilm eradication efficacy against biofilm-forming *Bacillus cereus* ATCC 14579.

To assess the biofilm eradication efficacy in accordance with the method published by M. Kwon et al. (Food Sci Biotechnol 26 (4): 1103-1111, 2017), *Bacillus cereus* was used to form a biofilm on a 96-well plate (Well plate; polystyrene, corning). Then, the biofilm eradication efficacy of BAL200 was assessed in accordance with the method published by Wu et al. (Antimicrob Agents Chemother 47:3407-3414, 2003). The experimental method is described below.

20 μl of the *Bacillus cereus* ATCC 14579 was added to 20 ml of the TSB medium containing 0.25% D-(+)-glucose and 1% sodium chloride and inoculated before an overnight culture at 37° C. The culture solution was diluted with the TSB medium containing 0.25% D-(+)-glucose and 1% sodium chloride until the OD600 (absorbance at 600 nm) reached 0.01. Then, 200 μl of the diluted solution was dispensed into each well on a 96-well plate, and cultured at 30° C. for 48 hours. Following the additional culture, 220 μl of the phosphate-buffered saline (PBS) was used to wash off the *Bacillus cereus* biofilm from the 96-well plate three times. Then, 200 μl of the diluted pharmaceutical composition prepared in Example 2 (BAL200 concentration: 10 μg/ml, 20 μg/ml, 40 μg/ml, and 80 μg/ml) was added to each well for a 2 h response before 200 μl of 0.1% Safranin was used to determine the biofilm eradication efficacy. The antibacterial protein B4 solution of the same concentration was applied as the control group. According to this experimental result, *Bacillus* genus-specific antibacterial protein BAL200 demonstrated its efficacy to eradicate the *Bacillus cereus* biofilm as expected, as shown in Table 3.

TABLE 3

| | Concentration (μg/ml) | | | | |
|---|---|---|---|---|---|
| Item | 0 | 10 | 20 | 40 | 80 |
| Antibacterial protein BAL200 treatment | – | + | +++ | +++ | +++ |
| Antibacterial protein B4 treatment | – | – | + | ++ | ++ |

–: No activity; +: Mild activity; ++: Moderate activity; +++: Intense activity

This result establishes the superior biofilm eradication efficacy of antibacterial protein BAL200.

Example 5: Assessing immunogenicity of *Bacillus* genus-specific antibacterial protein BAL200

Using the pharmaceutical composition (5 mg/ml) prepared in Example 2, we conducted an in vitro T-cell proliferation assay to examine the immunogenicity.

In the T-cell proliferation assay, the human primary cell line PBMC was labelled with the fluorescent dye CFSE to examine the decrease in the fluorescence intensity via FACS. More specifically, the RPMI 1640 medium (Gibco 11875-093) with 10% fetal bovine serum was warmed to 37° C. for 1 h. Then, 5 ml of the warmed medium was placed in a 50 ml conical tube, to which 1 vial of PBMC (Zen-bio, SER-PBMC-F) thawed at 37° C. for 10 minutes was added. Following the centrifugation at 2,500 rpm for 3 minutes, the supernatant was removed to collect the cells. Then, 20 ml of a new RPMI 1640 medium pre-warmed to 37° C. for 1 hour was added to the cells, which were in turn stirred well. After that, above cell mixture was transferred to a cell culture T-flask (75T) and cultured for 2 days (37° C., 5% $CO_2$). Following the 2-day culture, 18 μl of DMSO was added to 1 vial of CFSE (Thermo, C34570) to prepare the working solution with a dye concentration of 5 mM. Meanwhile, the cultured solution was moved to a 50 ml conical tube and centrifuged at 2,500 rpm for 3 minutes. Following the centrifugation, the supernatant was removed, and 1 ml of PBS was added to prepare a cell suspension. Then, the cells were counted with a cell counter (Lunar). The cell number was adjusted to $1\times10^6$ cells/ml, and 1 μl of the prepared CFSE working solution was added and cultured at 37° C. for 20 minutes under a light-shielded condition. After the culture, a new RPMI 1640 medium pre-warmed at 37° C. for 1 hour was added in the volume ratio of 5 times before the incubation at 37° C. for 5 minutes under a light-shielded condition. Upon completion of the incubation, it was centrifuged at 2,500 rpm for 3 minutes, and the supernatant was removed. Then, 1 ml of a new RPMI 1640 medium pre-warmed at 37° C. for 1 hour was added to prepare a cell suspension. After that, the cell counter was used to count the cells. The cell number was adjusted to $2\times10^6$ cells/ml before the incubation in the incubator for 10 minutes or longer for stabilization. 500 μl of the stabilized cell suspension was dispensed into each well on a 24-well plate, and 25 μl of the diluted solution of the pharmaceutical composition (BAL200 concentration: 400 μg/ml) prepared in Example 2 was added to each well (BAL200 concentration: 10 μg/well). As the control group, the antibacterial protein B4 solution of the same concentration was added and cultured (37° C., 5% $CO_2$). Here, in the negative control, 25 μl of PBS was added to each well. In the positive control, 25 μl of Dynabead™ Human T-Activator CD3/CD28 (Gibco 11161D) washed with PBS was added to each well prior to the culture to assess the decrease in CFSE fluorescence intensity of parent cells and the increase in daughter cells on a daily basis via FACS. On day 3 of the culture, the positive control group's (Dynabead™ Human T-Activator CD3/CD28) daughter cells increased by 9.97%, whereas daughter cells increased by 0.44% in the case with addition of antibacterial protein BAL200, which was comparable to the 0.25% increase in the negative control group (PBS). This result indicates that the immunogenicity of antibacterial protein BAL200 in the human primary cell line, PBMC, was very low as outlined in Table 4.

TABLE 4

| Item | Day 1 | Day 3 |
|---|---|---|
| | Increase in daughter cells (%) | |
| Negative control group | 0.26 | 0.25 |
| Positive control group | 8.25 | 9.97 |
| Antibacterial protein B4 | 3.00 | 4.74 |
| Antibacterial protein BAL200 | 0.30 | 0.44 |

This result indicates that the immunogenicity of antibacterial protein BAL200 was reduced compared to the antibacterial protein B4.

Example 6: Assessing Therapeutic Effects of *Bacillus* Genus-Specific Antibacterial Protein BAL200 on *Bacillus* Infections Using the pharmaceutical composition (5 mg/ml) prepared in Example 2, we assessed the therapeutic effects of *Bacillus* genus-specific antibacterial protein BAL200 on the infections caused by *Bacillus* bacteria using the infected animal model.

In this example, *Bacillus cereus* and *Bacillus circulans* were used as the model pathogen for *Bacillus* infections. 5-week-old ICR mice [specific pathogen-free (SPF) grade] weighing around 20 g each were used as experimental animals. A total of 20 mice were assigned to two groups (10 mice per each group). Then, $1\times10^8$ cfu of *Bacillus cereus* and *Bacillus circulans* were administered to each mouse (i.e. $1\times10^8$ cfu/mouse) intravenously to induce infections. One group (treatment group) was given the pharmaceutical composition (5 mg/ml) prepared in Example 2, at the time point of 30 minutes, 12 hours and 24 hours after the bacterial challenging. The dosage was set to 25 mg/kg. To the other group (control group), only the formulation buffer (10 mM L-Histidine, 0.1% Polysorbate 80, 5% Sorbitol, pH 6.0) was administered, where the volume of the formulation buffer administered to each animal was equivalent to the mean volume of the pharmaceutical composition administered to the treatment group. As in the administration of the pharmaceutical composition, the formulation buffer was administered at the time point of 30 minutes, 12 hours and 24 hours after the bacterial challenging. For five days following the bacterial challenging, dead individuals were counted each day, and specific responses were checked twice daily in the morning and afternoon.

This experimental result proved the explicit therapeutic effects. As shown in Table 5 below, the dead individual count supports the definite effects on the improved survival rates of the administered pharmaceutical composition containing the *Bacillus* genus-specific antibacterial protein BAL200 of the present invention. Also, compared with the control group, where diverse specific responses including erythema of lid margin and decreased activity were observed, such specific responses were hardly observed in the treatment group.

TABLE 5

| Group | Dead individuals Days after bacterial challenging 1 | 2 | 3 | 4 | 5 | Dead individuals/ Tested individuals | Mortality rate (%) |
|---|---|---|---|---|---|---|---|
| Control | 0 | 1 | 2 | 1 | 0 | 4/10 | 40 |
| Treatment | 0 | 0 | 0 | 0 | 0 | 0/10 | 0 |

This result indicates the *Bacillus* genus-specific antibacterial protein BAL200 of the present invention is effective for the treatment of infections caused by *Bacillus* genus. Such therapeutic effects suggest the pharmaceutical composition containing *Bacillus* genus-specific antibacterial protein BAL200 is applicable to treating the infections caused by *Bacillus* genus, and also can be used in the same manner as conventional antibiotics for the treatment of infections caused by *Bacillus* genus.

Example 7: Assessing Lytic Activity of *Bacillus* Genus-Specific Antibacterial Protein BAL200 Against *Bacillus anthracis*

Using the pharmaceutical composition (5 mg/ml) prepared in Example 2, we assessed the lytic activity of *Bacillus* genus-specific antibacterial protein BAL200 against various *Bacillus anthracis* strains. The *Bacillus anthracis* strains used for this assessment of lytic activity were *Bacillus anthracis* Ames, *Bacillus anthracis* Sterne, *Bacillus anthracis* A0102, *Bacillus anthracis* 1890A Clean Earth, *Bacillus anthracis* A0341 and *Bacillus anthracis* A0402, as outline in Table 6 below.

TABLE 6

| Strain | Source |
|---|---|
| *Bacillus anthracis* Ames | MRIGlobal |
| *Bacillus anthracis* Sterne | MRIGlobal |
| *Bacillus anthracis* A0102 | MRIGlobal |
| *Bacillus anthracis* 1890A Clean Earth | MRIGlobal |
| *Bacillus anthracis* A0341 | MRIGlobal |
| *Bacillus anthracis* A0402 | MRIGlobal |

MRIGlobal: 425 Volker Boulevard Kansas City, MO 64110, USA

The turbidity reduction assay was used to assess the lytic activity. The experimental method of the turbidity reduction assay is described below. The bacteria were suspended in normal saline until the absorbance at 600 nm reached around 0.6~0.8. Then, 0.1 ml of the diluted solution (BAL200 concentration: 50 μg/ml) of the pharmaceutical composition prepared in Example 2 was added to the suspension (0.9 ml). After that, the absorbance at 600 nm was measured for 20 minutes.

According to this experimental result, *Bacillus* genus-specific antibacterial protein BAL200 exhibited the lytic activity against all *Bacillus anthracis* strains tested as expected. The experimental results are shown in FIGS. 8-13. In the turbidity reduction assay used to assess the lytic activity, rapid lytic activity was observed.

These results prove that the *Bacillus* genus-specific antibacterial protein BAL200 of the present invention is able to lyse and eventually kill *Bacillus anthracis* bacteria. This antibacterial property suggests the pharmaceutical composition containing *Bacillus* genus-specific antibacterial protein BAL200 is applicable to killing *Bacillus anthracis* bacteria in infections caused by *Bacillus anthracis*, and to treating such infections in the same manner as conventional antibiotics.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An antibacterial protein against *Bacillus* comprising the amino acid sequence of SEQ ID NO: 1.

2. The antibacterial protein of claim 1, wherein the antibacterial protein consists of the amino acid sequence of SEQ ID NO: 1.

3. The antibacterial protein of claim 1, wherein the antibacterial protein has lytic activity against *Bacillus.*

4. The antibacterial protein of claim 3, wherein the antibacterial protein has lytic activity against *Bacillus anthracis, Bacillus cereus, Bacillus circulans, Bacillus laevolacticus, Bacillus licheniformis, Bacillus megaterium*, and *Bacillus pumilus.*

5. The antibacterial protein of claim 1, wherein the antibacterial protein has no lytic activity against *Salmonella, Escherichia coli* (*E. coli*), *Enterococcus faecalis*, and *Staphylococcus aureus.*

6. A pharmaceutical composition for treating disease caused by *Bacillus* infection comprising the antibacterial protein of claim 1.

7. The pharmaceutical composition of claim 6, wherein the disease caused by *Bacillus* infection is selected from the group consisting of anthrax, food poisoning, bacteremia, septicemia, toxemia and cerebromeningitis.

8. The pharmaceutical composition of claim 6, wherein the antibacterial protein is presented at a concentration of 0.1-50 mg/mL.

9. The pharmaceutical composition of claim 6, wherein the pharmaceutical composition further comprises 10 mM L-Histidine.

10. The pharmaceutical composition of claim 6, wherein the pharmaceutical composition is used as food additives, antibiotics, disinfectants, and germicides.

11. A method of preparing the antibacterial protein of claim 1, wherein the method comprises:

(a) culturing BL21-pBAD-BAL200 cells, wherein the BL21-pBAD-BAL200 cells comprise a plasmid comprising the nucleic acid sequence of SEQ ID NO: 2;

(b) inducing the expression of the antibacterial protein; and (c) purifying the antibacterial protein.

12. The method of claim 11, wherein the antibacterial protein has a purity of at least 90%.

* * * * *